US00PP28335P3

(12) United States Plant Patent
White

(10) Patent No.: US PP28,335 P3
(45) Date of Patent: Aug. 29, 2017

(54) PEAR TREE NAMED 'PREMP52'

(50) Latin Name: *Pyrus communis*
Varietal Denomination: PremP52

(71) Applicant: Prevar Limited, Hastings (NZ)

(72) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 14/999,019

(22) Filed: Mar. 18, 2016

(65) Prior Publication Data

US 2016/0278256 P1 Sep. 22, 2016

Related U.S. Application Data

(60) Provisional application No. 62/177,647, filed on Mar. 20, 2015.

(51) Int. Cl.
*A01H 5/08* (2006.01)

(52) U.S. Cl.
USPC ..... Plt./176

(58) Field of Classification Search
USPC ..... Plt./176
See application file for complete search history.

(56) References Cited

PUBLICATIONS

PLUTO Plant Variety Database Feb. 8, 2017.*

* cited by examiner

*Primary Examiner* — Annette Para
(74) *Attorney, Agent, or Firm* — Michelle Bos Legal LLC

(57) ABSTRACT

A new and distinct pear tree named 'PremP52' is disclosed. The new variety is notable for its attractive yellow fruit with light red blush, long shelf life and crisp, firm texture.

2 Drawing Sheets

Latin name: *Pyrus communis.*
Variety denomination: 'PremP52'.

BACKGROUND OF THE VARIETY

The new variety of pear tree 'PremP52' was created in the course of a planned breeding program carried out at The New Zealand Institute for Plant and Food Research, Hawkes Bay, New Zealand. 'PremP52' originated as a result of a controlled cross of 'T002' (not patented) and 'Prem1P' (U.S. Plant Pat. No. 17,624). 'PremP52' was selected as a single plant from among a population of seedlings derived from the parents, and was selected for its fruit size, flavor and appearance. Asexual propagation by budding was first carried out in Nelson, New Zealand. The variety has since been observed over a number of asexually propagated generations, and has been found to remain true to type.

BRIEF DESCRIPTION OF THE PHOTOGRAPHS

DETAILED BOTANICAL DESCRIPTION OF THE VARIETY

Figure 1:
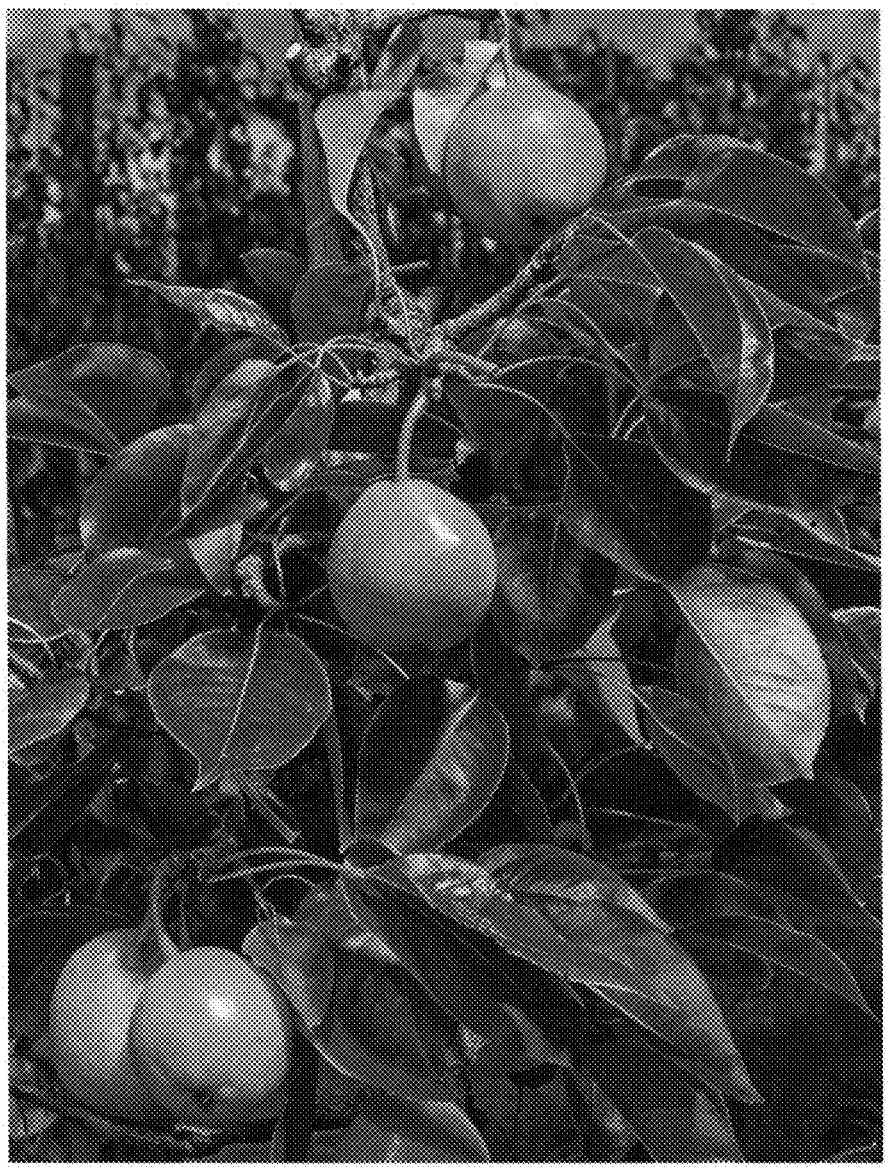
FIG. 1 shows the fruit and leaves of a 'PremP52' pear tree.
Figure 2:
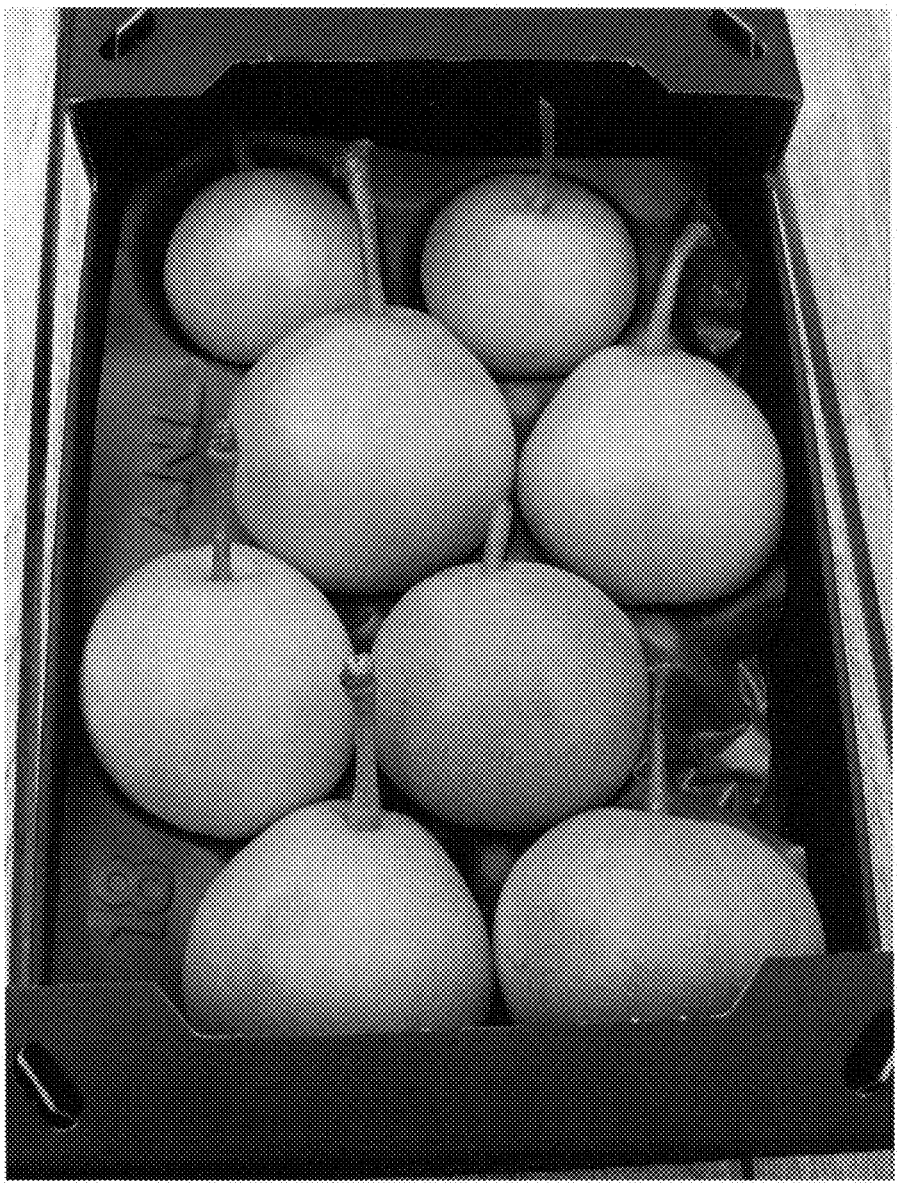
FIG. 2 shows fruit from a 'PremP52' pear tree.

The following detailed botanical description is based on observations made of five year old trees grown on 'Old Home×Farmingdale variety No. 87' rootstock (U.S. Plant Pat. No. 6,362) during the 2014 growing season at Parker, Wash. All colors are described according to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor.*—Strong.
- *Habit.*—Semi-upright.
- *Size.*—Height 9 feet, spread 5 feet.
- *Trunk.*—Diameter at 30 cm above graft union 10 cm.
- *Bark texture.*—Rough.
- *Bark color.*—Under color greyed-orange 168C, over color grey 201C, new growth — greyed-orange 177A.

Branch:
- *Size.*—Length 75 cm, diameter 1.5 cm at 1 m above graft union.
- *Crotch angle relative to trunk.*—90°.
- *Branch color.*—Greyed-orange 176D.

Dormant one-year-old shoot:
- *Size.*—Diameter 1 cm, length 7 cm.
- *Color.*—Greyed-orange 177A.
- *Internode length.*—4 cm.
- *Lenticels.*—Quantity 15 per square inch, color white 155C, diameter 0.5 cm.

Flowers:
- *Bud.*—Quantity per spur 7-8.
- *Bud length.*—0.7 cm.
- *Bud diameter.*—0.7 cm.
- *Outside color.*—White 155B.
- *Tip color.*—Greyed-purple 186C.
- *Flower diameter.*—4 cm.
- *Flower depth.*—1 cm.

*Quantity per cluster.*—7-8.
*Petal quantity per flower.*—10.
*Petal design.*—Double flowers ruffled.
*Petal margin.*—Ruffled.
*Petal length.*—2 cm.
*Petal width.*—2 cm.
*Petal upper surface color.*—White 155B.
*Petal lower surface color.*—White 155B.
*Quantity of sepals per flower.*—5.
*Sepal length.*—0.6 cm.
*Sepal width.*—0.5 cm.
*Sepal color.*—Yellow-green 145C.
*Pedicel length.*—5 cm.
*Pedicel diameter.*—0.1 cm.
*Pedicel color.*—Yellow-green 145B.
*Pistil.*—
*Stigma size.*—0.1 cm.
*Stigma color.*—Yellow-green 145B.
*Style size.*—0.5 cm.
*Style color.*—Yellow-green 145B.
*Ovary length.*—0.5 cm.
*Ovary width.*—0.4 cm.
*Ovary color.*—Yellow-green 145B.
*Stamen.*—Quantity of anthers per flower — 12.
*Anther size.*—0.1 cm.
*Filament length.*—0.5 cm.
*Pollen color.*—Red-purple 63B.
*Pollen abundancy.*—Medium.
*Bloom period.*—First bloom — March 23$^{rd}$; Full bloom — April 1$^{st}$.

Leaf:
*Attitude in relation to shoot.*—Upward.
*Blade margin.*—Serrated.
*Size.*—Length 9 cm, width 5 cm.
*Color.*—Upper surface yellow-green 146A.
*Apex with petiole.*—7.8 cm; diameter 0.2 cm.
*Color of upper surface.*—Yellow-green 146A.
*Color of lower surface.*—Yellow-green 147C.
*Attitude in relation to shoot.*—45°.

Petiole:
*Length.*—2.5 cm.
*Diameter.*—0.1 cm.
*Color.*—Yellow-green 147C.

Fruit:
*Shape in profile.*—Spherical.
*Position of maximum diameter.*—Near middle.
*Symmetry in longitudinal section.*—Mostly symmetrical.
*Profile of sides.*—Convex.
*Skin texture.*—Smooth with abundant lenticels.
*Background skin color.*—Green-yellow 1B.
*Overcolor.*—Red 42D, 20% to 30% coverage, intensity light.
*Russeting.*—Minimal to none.
*Stalk size.*—Thick, very long.
*Stalk curvature.*—Straight.
*Stalk color.*—Yellow-green 145A with greyed-red 181B at base.
*Flesh.*—Moderately firm, crisp, somewhat gritty, juicy.
*Flavor.*—Sweet with some tartness.
*Aroma.*—Delicate.

Diseases and pests: No significant resistance or susceptibility observed.

I claim:

1. A new and distinct pear tree substantially as shown and described herein.

* * * * *